Figure 1:
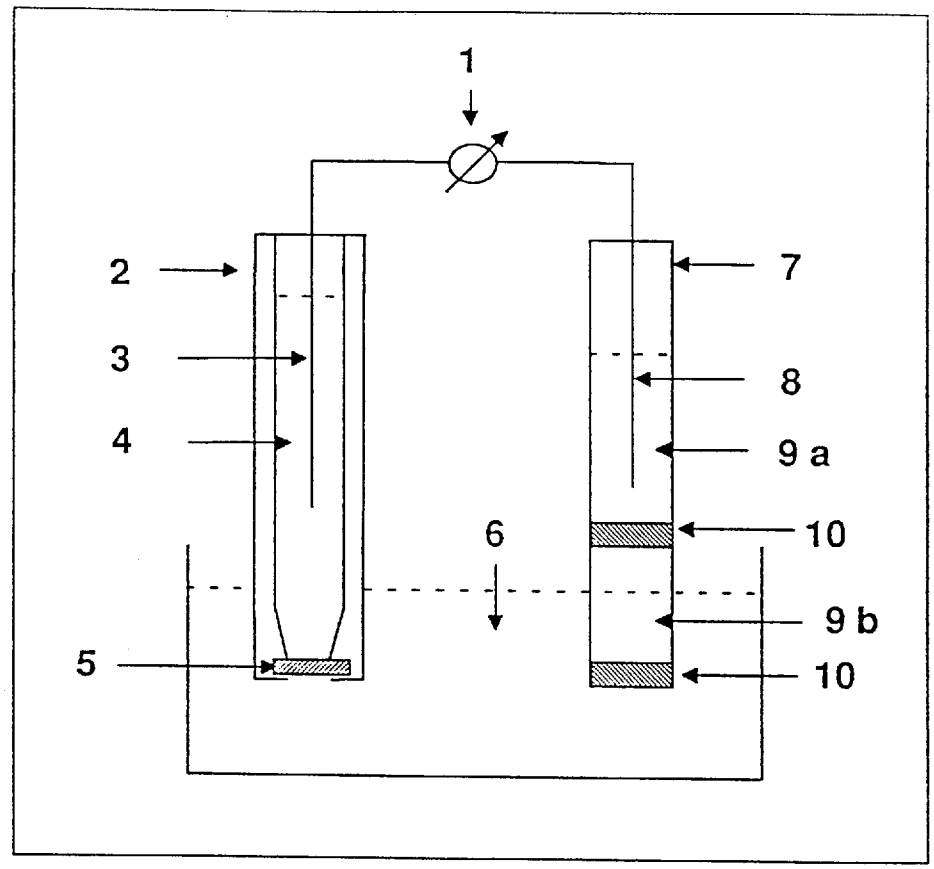

United States Patent [19]
Beckelmann et al.

[11] Patent Number: 5,863,972
[45] Date of Patent: Jan. 26, 1999

[54] RANDOMLY SEGMENTED THERMOPLASTIC POLYURETHANES AS MATRIX FOR ELECTROCHEMICAL ANALYSIS OF $CA^{++}$ IONS

[75] Inventors: Dirk Beckelmann, Saarbrücken, Germany; Joseph Berger, Basel, Switzerland

[73] Assignee: Chiron Diagnostics Corporation, E. Walpole, Mass.

[21] Appl. No.: 836,370

[22] PCT Filed: Nov. 2, 1995

[86] PCT No.: PCT/EP95/04300

§ 371 Date: Jul. 25, 1997

§ 102(e) Date: Jul. 25, 1997

[87] PCT Pub. No.: WO96/15443

PCT Pub. Date: May 23, 1996

[30] Foreign Application Priority Data

Nov. 14, 1994 [CH] Switzerland ............... 3409/94

[51] Int. Cl.$^6$ ............... C08J 3/00; C08K 3/20; C08L 75/00; C08L 83/00
[52] U.S. Cl. ............... 524/186; 128/635; 128/639; 128/642; 204/400; 204/413; 204/415; 204/418; 204/520; 422/82.03; 429/209; 429/250; 436/74; 524/588; 524/589; 524/590
[58] Field of Search ............... 524/186, 588, 524/589, 590; 128/635, 639, 642; 204/520, 400, 413, 415, 418; 422/82.03; 429/209, 250; 436/74

[56] References Cited

U.S. PATENT DOCUMENTS

| 4,816,130 | 3/1989 | Karakelle et al. ............... 204/403 |
| 5,035,791 | 7/1991 | Battilotti et al. ............... 204/415 |

FOREIGN PATENT DOCUMENTS

| 0125555 | 11/1984 | European Pat. Off. . |
| 62-65216 | 3/1987 | Japan . |
| 2086925 | 5/1982 | United Kingdom . |

OTHER PUBLICATIONS

Fiedler, U. et al., "Selectrode–The Universal Ion–Selective electrode"*Analytica Chimica Acta* 67 (1973) 179–193.

Oesch, U. et al., "Life Time of Neutral Carrier Based Ion–Selective Liquid–Membrane Electrodes" *Anal. Chem.* 52 (1980) 692–700.

Simon, W. et al., "Calcium–Selective Electrodes" *Ann. N.Y. Acad. Sci.* 307/52 (1978) 52–69.

Database WPI Week 8844, Derwent Publications Ltd., London, GB; AN 88–311565 & JP,A, 63229356 (Agency of Ind. Sci. Tech.) Sep. 26. 1988 (see abstract).

*Primary Examiner*—Patrick D. Niland
*Attorney, Agent, or Firm*—Arthur S. Morgenstern; Robert P. Blackburn

[57] ABSTRACT

Composition, comprising in homogeneous distribution A) at least one salt containing a lipophilic anion, B) a plasticiser-free thermoplastic randomly segmented polyurethane which is soluble in organic solvents, a polyurea or a polyurethane urea, which components are formed from a) 5–45% by weight of an aromatic, cycloaliphatic or linear aliphatic diisocyanate, b) 0–20% by weight of a linear or branched C2–C12alkylenediol or C2–C12alkylenediamine, c) 0–75% by weight of a polytetrahydrofuran or aminopropyl-terminated polytetrahydrofuran, d) 0–10% by weight of a polyethylene glycol or aminopropyl-terminated polyethylene glycol, e) 0–75% by weight of a polypropylene glycol or aminopropyl-terminated polypropylene glycol, which composition contains f) 15–95% by weight of a hydroxy-, hydroxypropyl- or aminopropyl-terminated polydimethylsiloxane, the percentages relating to the amount of polymer, and the sum of components a) to f) being 100, and C) a nonionic ionophore which forms a complex with $Ca^{++}$ ions. The invention also relates to an electrode for calcium analysis, containing said composition in the form of a membrane, to a process for the electrochemical analysis of $Ca^{++}$ ions in solution as well as to the use of this composition for the electrochemical analysis of $Ca^{++}$ ions.

35 Claims, 1 Drawing Sheet

RANDOMLY SEGMENTED THERMOPLASTIC POLYURETHANES AS MATRIX FOR ELECTROCHEMICAL ANALYSIS OF CA++ IONS

The invention relates to a composition consisting of a randomly segmented thermoplastic polyurethane, a polyurea or a polyurethane urea and a calcium ionophore, to an electrode for calcium analysis comprising said composition in the form of a membrane, to a process for the electrochemical analysis of Ca++ ions in solution as well as to the use of said composition for the electrochemical analysis of $Ca^{++}$ ions.

The electrochemical analysis of $K^+$ oder $Ca^{++}$ ions has been known for some time and is described, inter alia, in Analytica Chimica Acta 67 (1973). This publication in particular compares the properties of the valinomycin/ potassium electrode in a PVC matrix and in a polyurethane matrix. The membranes prepared from PVC must additionally contain at least one organic solvent or a plasticiser such as dioctyl phthalate to achieve the requisite electrochemical properties and the necessary mechanical properties such as flexibility and adhesion, e.g. on glass. Although the proposed polyurethane membranes have suitable mechanical properties even without the addition of a solvent or plasticiser, their electromechanical behaviour is markedly inferior to the system PVC/solvent. By adding dioctyl phthalate to the polyurethane matrix electrochemical properties can be achieved which are comparable to those of the system PVC/solvent.

U.S. Pat. No. 4,816,130 proposes the use of crosslinked polyurethanes having a hard segment component of 20 to 50% as membrane material in electrochemical sensors for blood analysis. The polyurethane membranes consist of a polyether glycol, a low molecular chain extender molecule such as butanediol, a diisocyanate and a trifunctional crosslinker, typically trimethylolpropane. The crosslinked polymers are no longer soluble in organic solvents. These membranes absorb from 50 to 120% of water, based on their dry weight.

Japanese patent specification No. Sho 62-65216 discloses the use of polyurethanes which have particularly good compatibility with blood and body tissue for in vivo examination. Said polyurethanes are block copolymers, one component of which consists of a hydroxyl-terminated ethylene oxide/polydimethylsiloxane/ethylene oxide triblock. The other components are diisocyanates, e.g. 4,4'-diphenylmethanediisocyanates, hydroxyl-terminated ethylene oxide/propylene oxide/ethylene oxide block copolymeres. An essential feature of these membranes is their low risk of causing thrombosis and that they have only a minor influence on the blood physiological functions. Nothing is known about their sensitivity, response time, selectivity and life span in $Ca^{++}$ sensors.

Although polyurethane membranes have already been proposed in the literature for use in electrochemical sensing, PVC is most often used as matrix material for $K^+$ and $Ca^{++}$ sensing. The advantages and disadvantages of this polymer are known and described, inter alia, by U. Oesch and W. Simon in Anal. Chem. 1980, 52, 692–700. The advantages are the rapid response time as well as the high sensitivity and selectivity. One of the disadvantages is that a plasticiser must be used in any case which is then slowly dissolved out during analysis, whereby in particular in in vivo analysis, undesirable substances may be left in the blood circulation. If continuous flow measurements are carried out, there may often be a particularly rapid loss of plasticiser or solvent which can interfere with the measurements, as sensitivity and response time may be altered thereby. The loss of plasticiser also has a negative effect on the life span of the electrode, which becomes brittle as loss increases and is no longer operable.

The present invention relates to a composition containing a plasticiser-free thermoplastic randomly segmented polyurethane which is soluble in organic solvents, a polyurea or a polyurethane urea as membrane material for the electrochemical $Ca^{++}$ sensors. The membrane has excellent response time, high sensitivity and selectivity. The adhesive properties on e.g. glass in an aqueous electrolyte are very good, and as no plasticiser is used, an in vivo analysis can be carried out without risk, if required. The flexibility of the polymer is still very good even at lower temperatures. This effect is achieved by the inherent soft segments in the polymer. At the same time this leads to a markedly improved life span. Even after many analyses, a susbstantially reproducible potential value and a virtually unaltered response time are obtained. The total response characteristics come very close to the ideal rectangular behaviour when chaning to higher to lower concentrations even after extended use.

In one of its aspects, the invention relates to a composition comprising in homogeneous distribution A) at least one salt containing a lipophilic anion,
B) a plasticiser-free thermoplastic randomly segmented polyurethane which is soluble in organic solvents, a polyurea or a polyurethane urea, which components are formed from
   a) 5–45% by weight of an aromatic, cycloaliphatic or linear aliphatic diisocyanate,
   b) 0–20% by weight of a linear or branched $C_2$–$C_{12}$alkylenediol or $C_2$–$C_{12}$alkylenediamine,
   c) 0–75% by weight of a polytetrahydrofuran or aminopropyl-terminated polytetrahydrofuran,
   d) 0–10% by weight of a polyethylene glycol or aminopropyl-terminated polyethylene glycol,
   e) 0–75% by weight of a polypropylene glycol or aminopropyl-terminated polypropylene glycol, which composition contains
   f) 15–95% by weight of a hydroxy-, hydroxypropyl- or aminopropyl-terminated poly-dimethylsiloxane, the percentages relating to the amount of polymer, and the sum of components a) to f) being 100, and
C) a nonionic ionophore which forms a complex with $Ca^{++}$ ions.

Ionophores are organic, natural or synthetic compounds containing several, usually alternating, electron-rich hetero atoms, typically S, N and, preferably, O in an open-chain or cyclic carbon chain and which are capable of selectively sequestering the ions to be analysed. The natural compounds are often macrocyclic compounds, typically valinomycin, which is capable of selectively binding potassium cations. Another typical example is nonactin. A large group of ionophores comprises the macrocyclic polyethers (crown ethers) which, depending on geometry and size, are capable of sequestering different metal cations. Further examples of ionophores are coronandenes, kryptandenes and calixarenes. A typical example of open-chain ionophores are the podandenes. Such ionophores are disclosed, inter alia, in U.S. Pat. No. 4,645,744.

The nonionic ionophore preferably contains an open-chain carbon chain containing several oxygen atoms and is most preferably (R,R)-N,N'-bis[11-ethoxycarbonyl-undecyl]-N,N',4,5-tetramethyl-3,6-dioxaoctanediamide, N,N-dicyclohexyl-N',N'-dioctadecyl-3-oxapentanediamide or N,N,N',N'-tetracyclohexyl-3-oxapentanediamide.

The composition contains the ionophore preferably in an amount of 0.01 to 10% by weight, more particularly of 0.1 to 5% by weight, based on the amount of polymer.

Preferred salts containing lipophilic anions are alkali metal salts and ammonium salts containing unsubstituted or substituted tetraphenylborates. Particularly preferred cations are $Li^+$, $Na^+$, $K^+$, $NH_4^+$, and the ammonium cations of primary, secondary and tertiary amines as well as quaternary ammonium cations containing 1 to 60 carbon atoms.

Some typical examples of ammonium cations are methyl-, ethyl-, propyl-, butyl-, hexyl-, octyl-, decyl-, dodecyl-, tetradecyl-, hexadecyl-, octadecyl-, dimethyl-, diethyl-, dibutyl-, butylmethyl-, dioctyl-, didoceyl-, dodecylmethyl-, trimethyl-, triethyl-, tripropyl-, tributyl-, trioctyl-, tridodecyl-, dodecyidimethyl-, didoecylmethyl-, tetramethyl-, tetraethyl-, tetrapropyl-, tetrabutyl-, tetrahexyl-, tetraoctyl-, tetradecyl-, tetradodecyl-, dodecyltrimethyl-, octyltrimetyl-, didodecyidimethyl-, tridodecylmethyl-, tetradecyltrimethyl- and octadecyltrimethylammonium. Quaternary ammonium salts are preferred, in particular those containing 4 to 48 carbon atoms.

Borate anions are preferably unsubstituted tetraphenylborate or tetraphenylborate which is substituted at the phenyl groups by one or more than one $C_1$–$C_4$alkyl, $C_1$–$C_4$alkoxy, halogen, e.g. F, Cl, Br or I, or trifluoromethyl.

Particularly preferred are sodium tetraphenylborate, sodium tetra(3,5-bistrifluoromethyl-phenyl)borate, potassium tetra(4-chlorophenyl)borate, tetrabutylammoniumtetraphenyl-borate and tetradodecylammonium(4-chlorophenyl)borate. The salts containing lipophilic anions act as negative charge equalisation for the $Ca^{++}$ cations to be analysed which cations diffuse into the active layer and are sequestered there. The salts containing lipophilic anions can also be salts of polymers containing acid or basic groups, typically polysulfonic acids or polycarboxylic acids.

The amount of salts containing lipophilic anions is preferably from 0.01 to 10% by weight, more particularly from 0.1 to 5% by weight, based on the amount of polymer.

A preferred composition is that comprising in homogeneous distribution

A) at least one salt containing a lipophilic anion,
B) a plasticiser-free thermoplastic randomly segmented polyurethane which is soluble in organic solvents and which is formed from
   a) 5–45% by weight of an aromatic, cycloaliphatic or linear aliphatic diisocyanate,
   b) 0–20% by weight of a linear or branched $C_2$–$C_{12}$alkylenediol,
   c) 0–75% by weight of a polytetrahydrofuran,
   d) 0–10% by weight of a polyethylene glycol,
   e) 0–75% by weight of a polypropylene glycol, which composition contains
   f) 15–95% by weight of a hydroxy- or hydroxypropyl-terminated polydimethylsiloxane, the percentages relating to the amount of polymer, and the sum of the components a) to f) being 100, and
C) a nonionic ionophore which forms a complex with $Ca^{++}$ ions.

Preferred are the diisocyanates are those selected from the group consisting of 1,6-bis[isocyanato]hexane, 5-isocyanato-3-(isocyanatomethyl)-1,1,3-trimethylcyclohexane, 1,3-bis[5-isocyanato-1,3,3-trimethylphenyl]-2,4-dioxo-1,3-diazetidine, 3,6-bis[9-isocyanatononyl]-4,5-bis (1-heptenyl)cyclohexene, bis[4-isocyanatocyclohexyl]methane, trans-1,4-bis[isocyanato] cyclohexane, 1,3-bis[isocyanatomethyl]benzene, 1,3-bis[1-isocyanato-1-methyl-ethyl]benzene, 1,4-bis[2-isocyanato ethyl]cyclohexane, 1,3-bis[isocyanatomethyl]cyclohexane, 1,4-bis[1-isocyanato-1-methylethyl]benzene, bis [isocyanato]isododecylbenzene, 1,4-bis[isocyanato] benzene, 2,4-bis[isocyanato]toluene, 2,6-bis[isocyanato] toluene, 2,4-/2,6-bis[isocyanato]toluene, N,N'-bis[3-isocyanato-4-methylphenyl]urea, 1,4-bis[3-isocyanato-4-methylphenyl]-2,4-dioxo-1,3-diazetidine, 1,3-bis[3-isocyanato-4-methylphenyl]-2,4,5-trioxoimidazolidine, bis [2-isocyanatophenyl]methane, (2-isocyanatophenyl)-(4-isocyanatophenyl)methane, bis[4-isocyanatophenyl] methane, 1,5-bis[isocyanato]naphthalene, or 4,4'-bis [isocyanato]-3,3'-dimethylbiphenyl.

The preferred diisocyanate is bis[4-isocyanatophenyl] methane (4,4'MDI), 2,4- or 2,6-bis-[isocyanato]toluene (TDI), 1,6-bis[isocyanato]hexane (HDI), 5-isocyanato-3-(isocyanatomethyl)-1,1,3-trimethylcyclohexane (IPDI) or bis[4-isocyanato-cyclohexyl]methane (MDI), or a mixture of these diisocyanates.

Typical examples of $C_2$–$C_{12}$alkylenediols are ethylene glycol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol.

Typical examples of $C_2$–$C_{12}$alkylenediamines are 1,2-ethylenediamine, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, 1,12-diaminododecane.

The hydroxy-, hydroxypropyl- or aminopropyl-terminated polydimethylsiloxane preferably has a molecular weight of 900 to 4500 dalton.

Preferred alkylenediols are ethylene glycol, 1,4-butanediol or 1,6-hexanediol.

Preferred alkylenediamines are ethylenediamine, 1,4-diaminobutane or 1,6-diaminohexane.

Minor amounts of alkylenetriols can also be used, typically 1,1,1-tris(hydroxymethyl)ethane in an amount of 0.1 to 5% by weight, based on the polymer. No measurable crosslinking takes place under these conditions and the polyurethane obtained remains soluble in organic solvents.

The polytetrahydrofuran or aminopropyl-terminated polytetrahydrofuran has a molecular weight of 1000 to 4500 dalton.

Polyethylene glycol or aminopropyl-terminated polyethylene glycol preferably has a molecular weight of 600 to 2000 dalton, and polypropylene glycol or aminopropyl-terminated polypropylene glycol has a molecular weight of 1000 to 4000 dalton.

A particularly preferred composition is that containing 4,4'-methylenediphenyidiisocyanate in an amount of 15–30% by weight, hydroxypropyl-terminated polydimethylsiloxane in an amount of 25–35% by weight, polytetrahydrofuran in an amount of 35–45% by weight and butanediol in an amount of 1–7% by weight, each based on the amount of polymer, the sum of the percentages of the individual components being 100.

Another also particularly preferred composition is that which contains 4,4'-methylenedi-phenyidiisocyanate in an amount of 8–28% by weight, hydroxypropyl-terminated polydi-methylsiloxane in an amount of 70–90% by weight and butanediol in an amount of 0.1–5% by weight, each based on the amount of polymer, the sum of the percentages of the individual components being 100.

The thermoplastic randomly segmented polyurethanes, polyureas or polyurethane ureas preferably have a molecular weight of 10,000 to 250,000, more preferably of 10,000 to 100,000 and, most preferably, of 10,000 to 30,000 dalton.

The glass transition temperature of the thermoplastic randomly segmented polyurethane, polyurea or polyurethane urea is preferably in the range from −125° C. to −40° C.

The composition is preferably obtained in the form of a solid polymer film or as a membrane, most preferably as a self-supporting membrane.

The preparation of such membranes can be carried out in per se known manner, typically by dissolving the composition in an organic solvent, then casting the solution to a film and, finally, removing the solvent. After removal of the solvent, the film can be peeled from the substrate and a self-supporting membrane is obtained.

Further possible processes for the preparation of the membrane are those known from coating technology, typically spin-coating, spraying or doctor coating processes.

Suitable solvents are ethers, esters, acid amides, ketones. Particularly suitable are readily volatile solvents, preferably tetrahydrofuran.

In addition to these processes, in which the composition is first dissolved and moulded, and the the solvent is then removed by evaporation, heat moulding processes may also be employed, as the composition consists of uncrosslinked thermoplastic material. Suitable processes are the extrusion, injection moulding, compression moulding or blow moulding methods known from thermoplastics processing.

The membrane can be transparent or slightly opaque. It is preferably transparent.

The invention also relates to an electrode for the analysis of $Ca^{++}$ ions, consisting of an outer assembly containing a) an aqueous $CaCl_2$ solution and an inner reference electrode, or b) a metal wire, and comprising the application of the novel composition a) in the form of a membrane or b) as a coating around the metal wire.

Suitable electrode assemblies are known from the literature, inter alia from Ann. N.Y. Acad. Sci. 307,52–62, 1978, and are commercially available.

The geometrical form of the electrode is per se irrelevant and depends on the environment of the fluid to be measured. They are typically spherical, cylindrical or rectangular in shape. The outer measurements can range from a few centimetres to miniaturised forms in the millimetre range. A correspondingly formed electrode can be used for in vivo and in vitro analysis.

The electrode can be constructed, for example, such that it contains the polymer film at the tip as self-supporting membrane and is filled inside e.g. with $CaCl_2$ solution of defined concentration in which an inner electrode is in turn immersed, typically an Ag/AgCl electrode. This electrode forms the half cell whose electromotive force can be measured, for example, against a standard calomel electrode, Ag/AgCl or normal hydrogen electrode. When the electrode sensitive to $Ca^{++}$ ions is immersed in a solution containing $Ca^{++}$ ions, a potential is obtained at the membrane which is proportional to the $Ca^{++}$ ion concentration present in the solution.

The concentration of the aqueous $CaCl_2$ solution to be measured is preferably from 0.001 to 0.5 molar.

The novel membrane preferably has a thickness of 50 $\mu$m to 500 $\mu$m.

Another basic electrode arrangement is also possible. In this arrangement a metal wire, e.g. made of silver, is coated with the novel composition. Coating is usually carried out by immersing the metal wire in the dissolved composition and then drying it. The coated metal wire is immersed in the measuring solution and forms the one half cell. A reference electrode, which is typically also immersed in the measuring solution, forms the second half cell. The value obtained is the potential difference between the $Ca^{++}$-containing sample and $Ca^{++}$-containing membrane.

Particularly suitable metals are silver, gold, palladium or platinum.

The invention also relates to a process for the analysis of $Ca^{++}$ ions in solution, which comprises a) placing the novel composition in the form of a membrane into an electrode or using a metallic wire coated with the composition as electrode, b) immersing the electrode with the membrane or the polymer film in a measuring solution and measuring the electrical voltage difference a gainst a standard electrode.

The process can be carried out batchwise or continuously, and the values obtained can be used for controlling processes.

The invention also relates to the use of the novel composition for the electrochemical analysis of $Ca^{++}$ ions in solutions.

The electrodes as well as the process for the analysis of $Ca^{++}$ ions are particularly suitable for measuring body fluids such as blood, setm, saliva or urine, which measurement can be carded out in vivo or in vitro. The process can be used for the quality control of corresponding production processes wherein, for example, $Ca^{++}$ is added, and in environmental analysis, e.g. for the control of wastewater. In agriculture, the calcium content of soils and plants can be controlled.

A possible electrode assembly is shown in FIG. 1, in which:

1=commercial pH meter,
2=measuring half cell,
3=Ag/AgCl electrode,
4=internal reference solution, typically 0.1 of molar $CaCl_2$ solution,
5=$Ca^{++}$ selective membrane,
6=$Ca^{++}$-containing measuring solution,
7=reference half cell,
8=Ag/AgCl electrode,
9a=internal reference electrolyte solution, typically saturated KCl,
9b=internal reference electrolyte solution, typically 0.1 m of $NH_4NO_3$,
10=diaphragm.

The following Examples illustrate the invention.

A Preparation of the thermoplastic randomly segmented Dolvurethanes

EXAMPLE A1

A three-necked flask with stirrer is charged with 2.0 g of polytetrahydrofuran (PTHF) having an average molecular weight $M_n$ of 2000 g/mol, 2.74 g of hydroxypropyl-terminated polydimethylsiloxane (PPDMS) having an average molecular weight of 2740° g/mol, 0.13 g of 1,4-butanediol (BDO), and 0.013 g of diazabicyclooctane (DABCO) dissolved under nitrogen in 30 ml of dry (anhydrous) tetrahydrofuran. The mixture is heated to 60° C. and 0.88 g of 4,4'-methylenediphenyidiisocyanate (MDI) is added at this temperature. The mixture is allowed to react for 4 hours at 60° C. and then 0.15 g of MDI in 2 ml of tetrahydrofuran is added dropwise over 90 minutes. After a further 60 minutes, 1 ml of butanediol is added to the reaction solution, which is then allowed to react for a further 60 minutes. The polymer is precipitated by pouring the reaction solution into 800 ml of methanol. The precipitate is isolated by filtration and dried at 20° C. under vacuum. The crude product is dissolved again in 30 ml of tetrahydrofuran and the solution is poured into 800 ml of methanol. The product is isolated by filtration and dried at 20° C. under vacuum, affording 4.6 g of a colouriess polymer, corresponding to 78% of theory. The procedure of Example 1 is repeated in Examples A2 to A4, but using the amounts listed in Table 1.

TABLE 1

Composition and characterisation of the polyurethanes (Amounts in g)

| Example | MDI | PPDMS M = 2740 | PTHF M = 2000 | BDO | Yield [%] | $T_g$ [°C.] | $M_n$ a) [g/mol] |
|---|---|---|---|---|---|---|---|
| A1 | 1.03 | 2.74 | 2.00 | 0.13 | 78 | −120 | 22800 |
| A2 | 1.15 | 2.74 | 4.35 b) | 0.18 | 82 | −120 | 17400 |
| A3 | 1.28 | 1.41 c) | 2.00 | 0.18 | 84 | −60 | 23500 |
| A4 | 1.15 | 5.48 | | 0.18 | 73 | −117 | 13800 | a) calculated from OH final group analysis
b) M = 4350
c) M = 940

EXAMPLE A5

A three-necked flask with stirrer is charged with 4.0 g of polytetrahydrofuran ($M_n$=2000 g/mol), 2.74 g of hydroxypropyl-terminated polydimethylsiloxane ($M_n$= 2740), 0.36 g of butanediol, and 0.013 g of diazabicyclooctane dissolved under inert conditions ($N_2$ atmosphere) in 50 ml of anhydrous tetrahydrofuran. At 60° C., 1.83 g of methylene-dicyclohexyldiisocyanate are added. After a reaction time of 4 h, 1 ml of butanediol is added to the reaction solution and the mixture is allowed to react for a further 60 minutes.

The polymer solution is poured into 1200 ml of methanol to precipitate the polymer, which is then isolated by filtration and dried at 20° C. under vacuum. The product obtained is dissolved again in 50 ml of tetrahydrofu ran, precipitated from 1200 ml of methanol, isolated by filtration and dried, affording 6.6 g (74% of theory) of a colourless product. The glass transition temperature $T_g$ is −118° C. and the average molecular weight $M_n$ is 40,000 g/mol.

EXAMPLE A6

Preparation of segmented polyureas and polyurethanepolyureas

A three-necked flask with KPG stirrer is charged with 4.4 g of aminopropyl-terminated polytetrahydrofuran ($M_n$= 2200 g/mol), 2.4 g of aminopropyl-terminated polydimethyl-siloxane ($M_n$=2400), 0.045 g of butanediol dissolved under inert conditions ($N_2$ atmosphere) in a mixture of 40 ml of anhydrous tetrahydrofuran and 10 ml of anhydrous dimethyl formamide. A solution of 0.875 g of methylenediphenyldiisocyanate in 15 ml of tetrahydrofuran is added dropwise at room temperature. After a reaction time of 2 h, 0.010 g of dibutyl tin dilaurate is a dded to the reaction solution, which is then allowed to react for a further 2 h at 60° C. 1 ml of butanediol is added and the mixture is allowed to react for afurther 1 h.

The polymer solution is poured into 1200 ml of acetonitrile to precipitate the polymer, which is then isolated by filtration and dried at 20° C. under vacuum. The product obtained is dissolved a gain in 50 ml of tetrahydrofuran, precipitated from 1200 ml of acetonitdie, isolated by filtration and dried, affording 6.0 g (77% of theory) of a colouless product. The glass transition temperature $T_g$ is −122° C. and the average molecular weight $M_n$ is 66,000 g/mol.

EXAMPLE A7 is carried out in general accordance with the procedure of Example A6, but using the following amounts:

0.75 g of methylenediphenyl dpsocyanate 2.40 g of aminopropyl-terminated polydimethylsiloxane ($M_n$=2400), 4.40 g of aminopropyl-terminated polytetrahydrofuran ($M_n$=2200 g/mol)

B Preglaration of the polymer films (membranes) for the $Ca^{++}$ selective electrode

EXAMPLE B1

0.3 g of the polyurethane of Example A1 is dissolved in 3 ml of tetrahydrofuran. To this solution are added 0.004 g of potassium tetra(4-chlorophenyl)borate and 0.010 g of calcium ionophore (R,R)-N,N'-bis[11-ethoxycarbonylundecyl]-N,N',4,5-tetra-methyl-3,6-dioxaoctane The solution is poured into an O-ring resting snugly on a glass plate and having a diameter of 31 mm, and the solvent is allowed to evaporate at room temperatur over 24 h, affording a transparent and flexible polymer film of 0.20 to 0.25 mm.

EXAMPLES B2 to B4

The procedure of Example B1 is repeated for the polymers of Examples A2 to A4, to give the polymer films B2 to B4. The procedure of Example B1 is also repeated for the polymers of Examples A5 to A7, to give the polymer films B8 to B10.

EXAMPLE B5

The procedure of Example B1 is repeated, but using 0.3 g of the polyurethane of Example A3, 0.010 g of the ionophore N,N-dicyclohexyl-N',N'-dioctadecyl-3-oxapentane-diamide and 0.003 g of potassium tetra(4-chlorophenyl)borate.

EXAMPLE B6

The procedure of Example B1 is repeated, but using 0.3 g of the polyurethane of Example A4, 0.010 g of the ionophore N,N-dicyclohexyl-N',N'-dioctadecyl-3-oxapentane-diamide and 0.003 g of potassium tetra(4-chlorophenyl)borate.

EXAMPLE B7

The procedure of Example B1 is repeated, but using 0.3 g of the polyurethane of Example A4, 0.010 g of the ionophore N,N,N',N'-tetracyclohexyl-3-oxapentane-diamide and 0.005 g of potassium tetra(4-chlorophenyl) borate.

COMPARISON EXAMPLE V1

The procedure of Example B1 is repeated, but replacing the polyurethane of Example A1 with 0.126 g of PVC using 0.174 g of o-nitrophenyloctyl ether as plasticiser.

Circular pieces having a diameter of 6 mm are cut from the polymer films of Examples B1 to B10 and V1 and placed in electrode shells of the IS 561 type, supplied by Philips.

The electrode properties are measured against an Ag/AgCl electrode and are shown in Table 2.

TABLE 2

Characterisation of the electrode properties at 21° C.

| Example | Sensitivity mV/log($Ca^{++}$) | Response time [s] | Selectivity coefficient log K($Ca^{++}$,$M^+$) | | | |
|---|---|---|---|---|---|---|
| | | | $Mg^{++}$ | $Li^+$ | $K^+$ | $Na^+$ |
| B1 | 29.2 | 70–200 | −3.7 | −3.1 | −4.1 | −3.8 |
| B2 | 29.1 | 60 | −3.8 | −3.0 | −3.9 | −4.1 |
| B3 | 29.4 | 20–30 | −3.8 | −3.4 | −3.7 | −4.2 |
| B4 | 29.0 | 30–60 | −3.9 | −3.8 | −4.0 | −4.2 |
| B5 | 30.7 | 30–45 | −5.6 | −3.1 | −4.3 | −4.0 |
| B6 | 26.7 | 30–45 | −4.1 | −3.9 | −3.7 | −3.8 |
| B7 | 25.5 | 20–30 | −3.8 | −3.6 | −3.7 | −3.7 |
| B8 | 27.8 | 30–90 | −3.7 | −2.8 | −3.2 | −3.7 |
| B9 | 28 | 20–45 | −3.6 | −2.4 | −3.1 | −3.5 |
| B10 | 27.3 | 60–90 | −3.6 | −2.5 | −3.2 | −3.6 |
| V1 | 28.9 | 70–200 | −4.0 | −3.3 | −3.7 | −3.7 |

Explanations for Table 2

The sensitivity in mV/log ($Ca^{++}$) is determined with calibration solutions. The calibration solutions contain 0.25, 0.5, 1.0, 2.5 and 5.0 of $CaCl_2$ mmol/liter and are charged with 159.25, 158.5, 157, 152.5 and 145 of NaCl mmol/liter for the adjustment of a constant ionic strength (160 mmol/liter).

The measurement of the response time is carried out by measuring the time until a stationary potential value is reached when changing three times from a 0.01 molar $CaCl_2$ solution to a 0.001 molar $CaCl_2$ solution. The range of the 6 values obtained is indicated.

The selectivity coefficients are determined from the potential values for pure 0.1 molar $CaCl_2$, $MgCl_2$, KCl and LiCl solutions. The selectivity against $Na^+$ is determined with calibration solutions of 5, 2.5, 1, 0.5, 0.1, 0.01, 0.001, 0.0001, 0.00001 and 0.000001 of $CaCl_2$ mmol/liter and a constant 150 of NaCl mmol/liter.

What is claimed is:

1. A composition, comprising in homogeneous distribution

A) at least one salt containing a lipophilic anion,

B) a plasticiser-free thermoplastic randomly segmented polyurethane which is soluble in organic solvents, a polyurea or a polyurethane urea, which components are formed from
   a) 5–45% by weight of an aromatic, cycloaliphatic or linear aliphatic diisocyanate,
   b) 0–20% by weight of a linear or branched $C_2$–$C_{12}$alkylenediol or $C_2$–$C_{12}$alkylenediamine,
   c) 0–75% by weight of a polytetrahydrofuran or aminopropyl-terminated polytetrahydrofuran,
   d) 0–10% by weight of a polyethylene glycol or aminopropyl-terminated polyethylene glycol,
   e) 0–75% by weight of a polypropylene glycol or aminopropyl-terminated polypropylene glycol, which composition contains
   f) 15–95% by weight of a hydroxy-, hydroxypropyl- or aminopropyl-terminated polydimethylsiloxane, the percentages relating to the amount of polymer, and the sum of components a) to f) being 100, and C) a nonionic ionophore which forms a complex with $Ca^{++}$ ions.

2. A composition according to claim 1, wherein the aminopropyl-terminated polydimethylsiloxane has a molecular weight of 900 to 4500 dalton.

3. A composition according to claim 1, wherein the alkylenediamine is ethylenediamine, 1,4-diaminobutane or 1,6-diaminohexane.

4. A composition according to claim 1, wherein the aminopropyl-terminated polytetrahydrofuran has a molecular weight of 1000 to 4500 dalton.

5. A composition according to claim 1, wherein the aminopropyl-terminated polyethylene glycol has a molecular weight of 600 to 2000 dalton.

6. A composition according to claim 1, wherein the aminopropyl-terminated polypropylene glycol has a molecular weight of 1000 to 4000 dalton.

7. A composition according to claim 1, comprising in homogeneous distribution

A) at least one salt containing a lipophilic anion,

B) a plasticiser-free thermoplastic randomly segmented polyurethane which is soluble in organic solvents, a polyurea or a polyurethane urea, which components are formed from
   a) 5–45% by weight of an aromatic, cycloaliphatic or linear aliphatic diisocyanate,
   b) 0–20% by weight of a linear or branched $C_2$–$C_{12}$alkylenediol,
   c) 0–75% by weight of a polytetrahydrofuran,
   d) 0–10% by weight of a polyethylene glycol,
   e) 0–75% by weight of a polypropylene glycol, which composition contains
   f) 15–95% by weight of a hydroxy-, hydroxypropyl-terminated polydimethylsiloxane, the percentages relating to the amount of polymer, and the sum of components a) to f) being M 100, and C) a nonionic ionophore which forms a complex with $Ca^{++}$ ions.

8. A composition according to claim 1, wherein the nonionic ionophore is an open-chain carbon chain containing several oxygen atoms.

9. A composition according to claim 8, wherein the ionophore is (R,R)-N,N'-bis[11-ethoxycarbonylundecyl]-N,N',4,5-tetramethyl-3,6-dioxaoctanediamide, N,N-dicyclohexyl-N',N'dioctadecyl-3-oxapentanediamide or N,N,N',N'-tetracyclohexyl-3-oxapentanediamide.

10. A composition according to claim 1, comprising the ionophore in an amount of 0.01 to 10% by weight, based on the amount of polymer.

11. A composition according to claim 10, comprising the ionophore in an amount of 0.1 to 5% by weight, based on the amount of polymer.

12. A composition according to claim 1, wherein the salt containing a lipophilic anion is an alkali metal salt or ammonium salt, and the anion contains unsubstituted or substituted tetraphenylborate.

13. A composition according to claim 12, wherein the cations are $Li^+$, $Na^+$, $K^+$, $NH_4^+$ and ammonium cations of primary, secondary and tertiary amines as well as quaternary ammonium cations containing 1 to 60 carbon atoms.

14. A composition according to claim 12, wherein the borate anion is tetraphenylborate whose phenyl groups are unsubstituted or substituted by one or more than one $C_1$–$C_4$alkyl, $C_1$–$C_4$alkoxy, halogen or trifluoromethyl.

15. A composition according to claim 14, wherein the borate anion is sodium tetraphenylborate, sodium tetra(3,5-bistrifluoromethylphenyl)borate, potassium tetra(4-chlorophenyl)borate, tetrabutylammoniumtetraphenylborate and tetradodecylammonium(4-chlorophenyl)borate.

16. A composition according to claim 12, wherein the amount of salts containing lipophilic anions is from 0.01 to 10% by weight, based on the amount of polymer.

17. A composition according to claim 1, wherein the diisocyanate is bis[4-isocyanatophenyl]methane (4,4' MDI), 2,4-or 2,6-bis[isocyanato]toluene (TDI), 1,6-bis[isocyanato] hexane (HDI), 5-isocyanato-3-(isocyanatomethyl)-1,1,3-trimethylcyclohexane (IPDI) or bis[4-isocyanatocyclohexyl]methane (MDI), or a mixture of these diisocyanates.

18. A composition according to claim 7, wherein the hydroxy- or hydroxypropyl-terminated polydimethylsiloxane has a molecular weight of 900 to 4500 dalton.

19. A composition according to claim 7, wherein the alkylenediol is ethylene glycol, 1,4-butanediol or 1,6-hexanediol.

20. A composition according to claim 7, wherein the polytetrahydrofuran has a molecular weight of 1000 to 4500 dalton.

21. A composition according to claim 7, wherein the polyethylene glycol has a molecular weight of 600 to 2000 dalton.

22. A composition according to claim 7, wherein the polypropylene glycol has a molecular weight of 1000 to 4000 dalton.

23. A composition according to claim 7, containing 4,4'-methylenediphenyidiisocyanate in an amount of 15–30% by weight, hydroxypropyl-terminated polydimethylsiloxane in an amount of 25–35% by weight, polytetrahydrofuran in an amount of 35–45% by weight and butanediol in an amount of 1–7% by weight, each based on the amount of the polymer, the sum of the percentages of the individual components being 100.

24. A composition according to claim 7, containing 4,4'-methylenediphenyidiisocyanate in an amount of 8–28% by weight, hydroxypropyl-terminated polydimethylsiloxane in an amount of 70–90% and butanediol in an amount of 0.1–5% by weight, each based on the amount of polymer, the sum of the percentages of the individual components being 100.

25. A composition according to claim 1, wherein the thermoplastic randomly segmented polyurethane, polyurea or polyurethane urea has a molecular weight of 10,000 to 250,000.

26. A composition according to claim 25, wherein the thermoplastic randomly segmented polyurethane, polyurea or polyurethane urea has a molecular weight of 10,000 to 100,000.

27. A composition according to claim 25, wherein the thermoplastic randomly segmented polyurethane, polyurea or polyurethane urea has a molecular weight of 10,000 to 30,000.

28. A composition according to claim 1, wherein the thermoplastic randomly segmented polyurethane, polyurea or polyurethane urea has a glass transition temperature from −125° C. to −40° C.

29. A composition according to claim 1, which is in the form of a membrane.

30. A composition according to claim 29, which is in the form of a self-supporting membrane.

31. A composition according to claim 29, wherein the membrane has a thickness of 50 $\mu$m to 500 $\mu$m.

32. An electrode for the analysis of $Ca^{++}$ ions, consisting of an outer assembly containing a) an aqueous $CaCl_2$ solution and an inner reference electrode, or b) a metal wire, the novel composition of claim 1 being applied a) in the form of a membrane or b) as a coating around the metal wire.

33. An electrode for the analysis of $Ca^{++}$ ions according to claim 32, wherein the aqueous $CaCl_2$ solution has a concentration of 0.001 to 0.5 molar.

34. A process for the analysis of $Ca^{++}$ ions in solution, which comprises
  a) placing the novel composition of claim 1 in the form of a membrane into an electrode or using a metallic wire coated with the composition of claim 1 as electrode,
  b) immersing the electrode with the membrane or polymer film in a measuring solution and measuring the electrical voltage difference against a standard electrode.

35. The composition according to claim 1 for use in the electrochemical analysis of $Ca^{++}$ ions in solutions.

* * * * *